(12) United States Patent
Menegon et al.

(10) Patent No.: US 9,072,461 B2
(45) Date of Patent: Jul. 7, 2015

(54) POSTURE OBSERVER FOR ERGONOMIC OBSERVATION, POSTURE ANALYSIS AND RECONSTRUCTION

(75) Inventors: Nilton Luiz Menegon, São José dos Campos/SP (BR); Daniel Cleiton Quartim Campos, São José dos Campos/SP (BR); Luiz Antonio Tonin, São Carlos/SP (BR); Marina Greghi Sticca, São Carlos/SP (BR); Jerusa Barbosa Guarda de Souza, São Carlos/SP (BR); Lucas Alves Volpes, São Carlos/SP (BR); Talita Naiara Rossi, São Carlos/SP (BR)

(73) Assignee: EMBRAER S.A., São José dos Campos (BR)

( * ) Notice: Subject to any disclaimer, the term of this patent is extended or adjusted under 35 U.S.C. 154(b) by 535 days.

(21) Appl. No.: 13/404,960

(22) Filed: Feb. 24, 2012

(65) Prior Publication Data

US 2012/0265104 A1     Oct. 18, 2012

Related U.S. Application Data

(60) Provisional application No. 61/446,900, filed on Feb. 25, 2011.

(51) Int. Cl.
 *A61B 5/00* (2006.01)
 *A61B 5/103* (2006.01)
(52) U.S. Cl.
 CPC ........................... *A61B 5/103* (2013.01)

(58) Field of Classification Search
 CPC ................................. A61B 5/11; A61B 5/103
 USPC ................................................... 600/587, 595
 See application file for complete search history.

(56) References Cited

U.S. PATENT DOCUMENTS

| | | | |
|---|---|---|---|
| 6,865,581 B1 | 3/2005 | Cloninger, Jr. et al. | |
| 7,029,031 B2 | 4/2006 | Moisel et al. | |
| 7,877,706 B2 * | 1/2011 | Albertson et al. | 715/863 |
| 8,269,834 B2 * | 9/2012 | Albertson et al. | 348/152 |
| 8,801,637 B2 * | 8/2014 | Nishibayashi | 600/595 |
| 8,831,299 B2 * | 9/2014 | Kurtz et al. | 382/128 |
| 2003/0181830 A1 | 9/2003 | Guimond et al. | |

FOREIGN PATENT DOCUMENTS

WO     2010/122174 A1     10/2010

OTHER PUBLICATIONS

Actogram Kronos, Notice d'utilisation, Version 1.1, Octares Editions (2010).

(Continued)

*Primary Examiner* — Max Hindenburg
(74) *Attorney, Agent, or Firm* — Nixon & Vanderhye P.C.

(57) ABSTRACT

A system and method for analysis of steps of action of a person in activity in an environment with potential occlusion and without the need to use of invasive equipment. Non-limiting implementations use posture registration and postural analysis based on an observation protocol that allows reconstruction, in a digital human simulation environment, of the adopted postures observed in a real time situation or by video.

14 Claims, 8 Drawing Sheets

(56) References Cited

OTHER PUBLICATIONS

CAPTIV-L2100, Task Analysis Software, www.teaergo.com (2010).
CAPTIV-L7000, www.teaergo.com (2010).
"The Observer® XT," www.noldus.com (retrieved 2012).
www.ergonomics.co.uk (retrieved 2010).
de Souza, Jerusa Barbosa Guarda et al., "Parameters related to passengers' comfort: a research on the practices adopted by seat manufacturers," (Producão, Feb. 14, 2012 EPub).
Karhu, Osmo et al., "Observing working postures in industry: Examples of OWAS application," Applied Ergonomics, 12.1, pp. 13-17 (Mar. 1981).
McAtamney, Lynn et al., "Reducing the Risks of Work Related Upper Limb Disorders: A guide and methods," Institute for Occupational Ergonomics, University of Nottingham NG7 2RD (1992).
McAtamney, Lynn et al., "RULA: a survey method for investigation of work-related upper limb disorders," Applied Ergonomics, vol. 24, No. 2, pp. 91-99 and RULA Employee Assessment Worksheet (Apr. 1993).

* cited by examiner

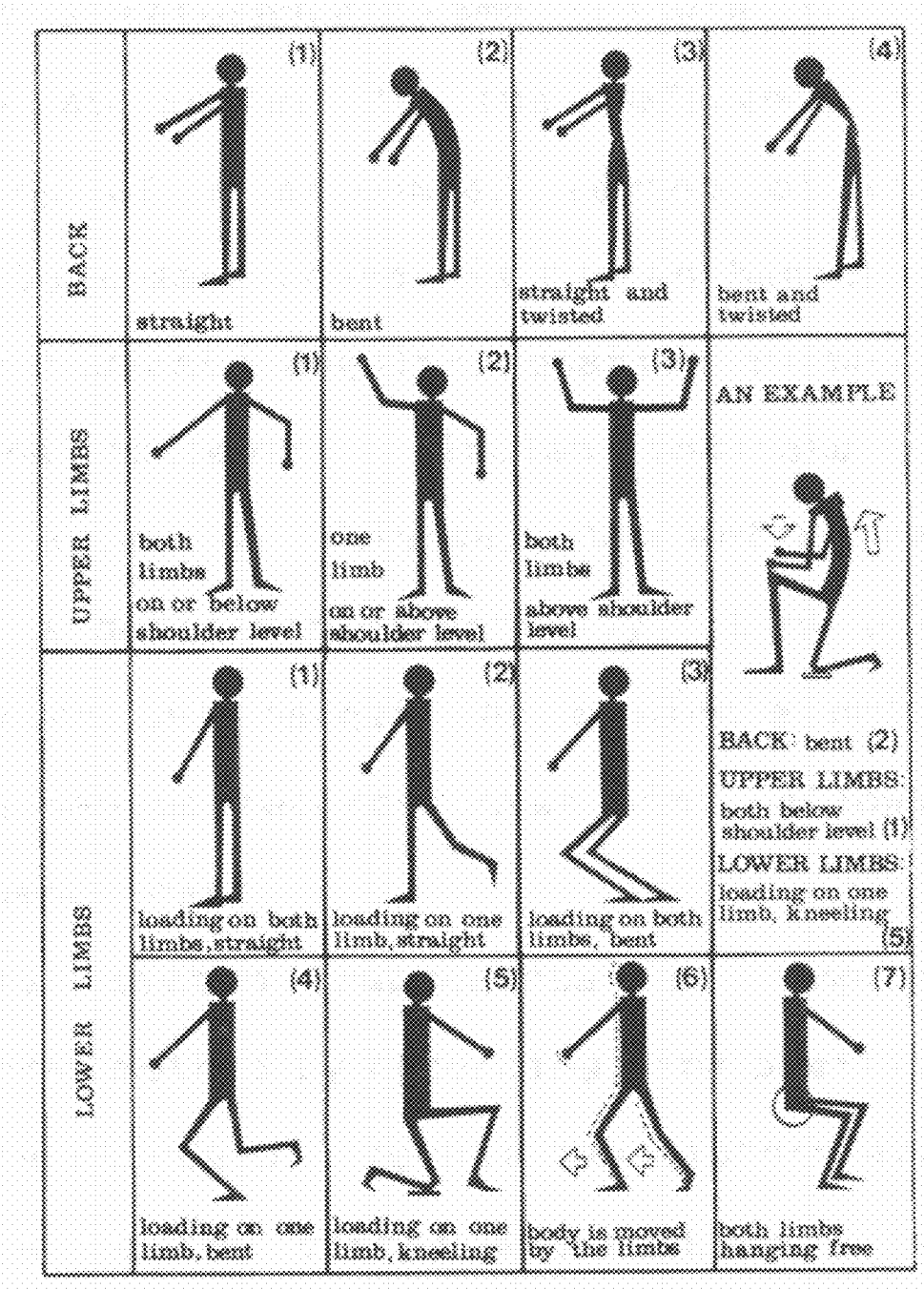
Figure 1: OWAS protocol (prior art)

Figure 2A (prior art)

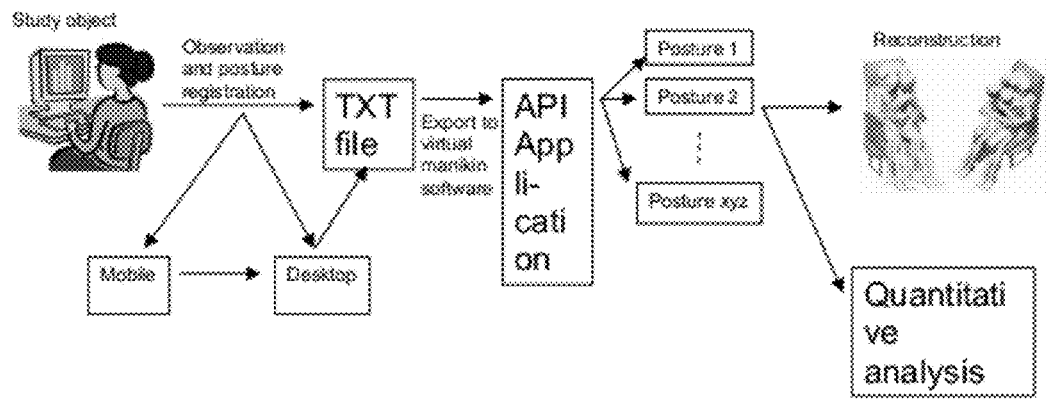
Figure 3: Flowchart
Figure 4: Example of posture observation protocol – Print version

Figure 5: Example of posture observation protocol –Desktop version
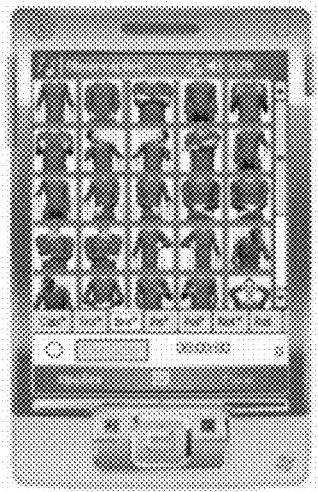
Figure 6: Example of posture observation protocol –Mobile version

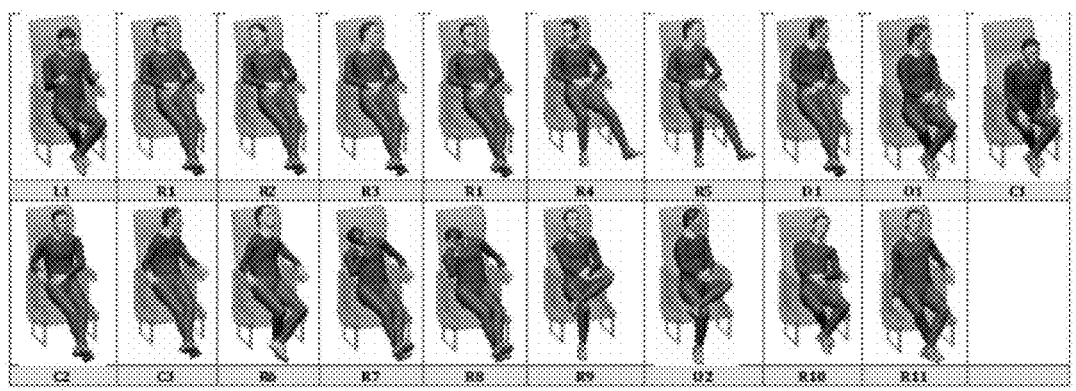
Figure 7: Steps of action
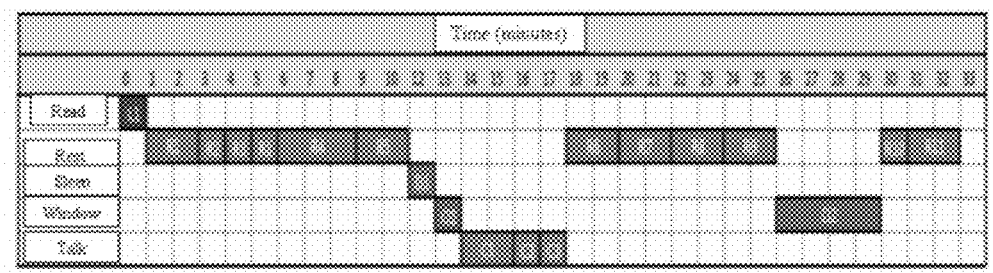
Figure 8: Postures and activities with respect to time

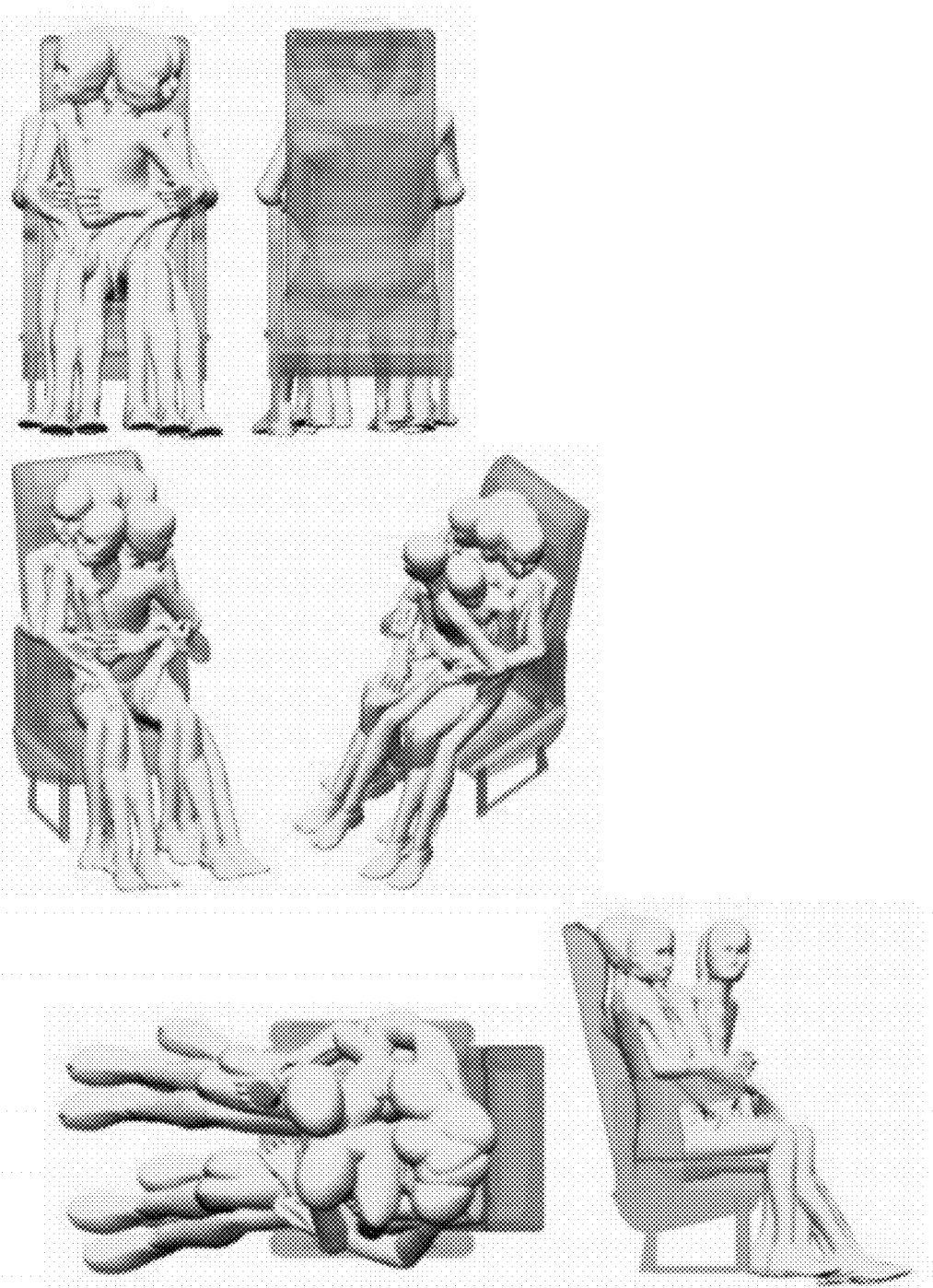
Figure 9: Example Volumes of postures

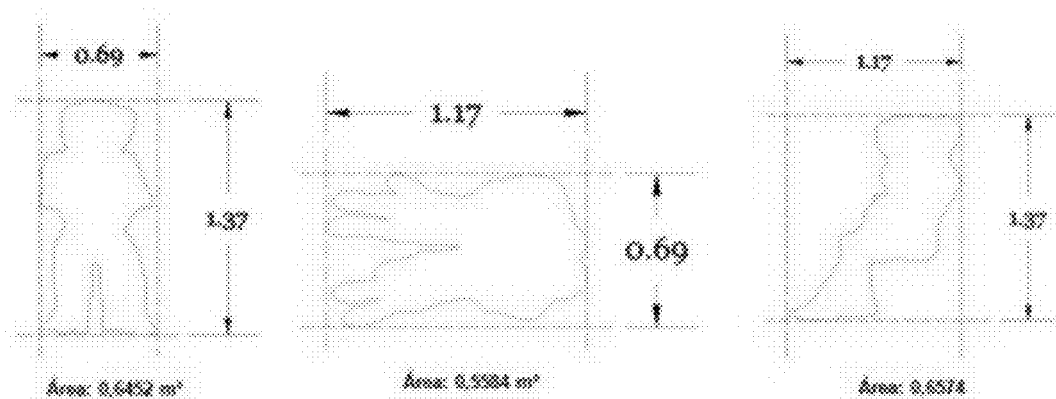
Figure 10: Areas created from volumes of postures

POSTURE OBSERVER FOR ERGONOMIC OBSERVATION, POSTURE ANALYSIS AND RECONSTRUCTION

CROSS-REFERENCES TO RELATED APPLICATION

This application claims benefit of priority from provisional application No. 61/446,900 filed Feb. 25, 2011, the entire contents of which is incorporated herein by reference.

STATEMENT REGARDING FEDERALLY SPONSORED RESEARCH OR DEVELOPMENT

None.

FIELD

The technology herein relates to system and method for observation, postural analysis and reconstruction, and more particularly to a noninvasive system and method for ergonomics and behavioral analysis in different environments, for example means of transportation including but not limited to aircraft.

BACKGROUND AND SUMMARY

Air travel has made the world a smaller place than ever. You can board an airplane and be on the other side of the world in half a day. People are increasingly travelling to faraway places for business and pleasure. No longer are international flights and long distance trains limited to businessmen and the very wealthy.

The increase in travel has put pressure on travel companies such as airlines to compete on price as well as quality. For example, flying business class can cost many times what a coach seat costs. Some travelers are willing to pay more for increased comfort—especially on long intercontinental flights. Such consumers of transportation can be very demanding. It is hard for manufacturers and service providers to live up to their expectations without risk of running out of the market. Consequently, manufacturers of means of transportation can no longer focus only the performance of vehicles and equipment. Lately, manufacturers have also become increasingly concerned with passenger and crew comfort.

For that reason, manufacturers have been observing and studying how passengers and crew act and react during the entire trip. In order to correctly dimension and design the space occupied by passengers and crew while they are traveling, it is useful to observe and record such observations of exposures, behaviors and actions the passengers and crew carry out over time.

There is thus a long felt need to produce reliable records of each step of the actions performed by a person in an environment, for example passengers inside an airplane as they are being transported. The aim of these records is to allow analysis of the statistics of passenger behavior and to reconstruct the steps of action over time through simulation in virtual environments using virtual manikins. In addition, it is possible to determine parameters for designing interiors of vehicles such as airplanes based on the space that passengers occupied during the performance of an activity.

Generally speaking, traditional methods and systems for capturing and recording person behavior can be divided into "invasive" and "non-invasive" techniques.

Generally, invasive methods use sensors attached to the object (subject) of observation to capture and record his movements. Such invasive techniques generally involve some type of physical interference or intervention to observe a person in activity. For example, one such technique determines the posture of a person by using at least one motion sensor with at least one measurement axis provided with an attachment means for rigidly connecting said motion sensor to the person. Another example technique acquires biomechanical data for use in postural analysis through the selection of markers on the actor's body, making it possible to analyze the positions of each body segment for biomechanical parameters and postural deviations.

Noninvasive methods include the use of classical protocol-based ergonomics by filming the object of observation, converting their movements on symbols and points, and triangulating these points. One such example technique detects the body position taken by passengers sitting in a seat of a vehicle based on the blockage of different light propagation paths. In particular, the head position and the inclination of a seat back rest can be detected. One challenge is to be able to analyze the entire posture of a person in a vehicle despite many potential occlusions that may prevent the full capture of the position of the different body segments of the passenger.

Another known technique performs job analysis by creating a list of job requirements and working conditions for a job for determining whether a worker can perform a job.

Some known systems and methods use classical ergonomics protocols for posture recording and postural analysis. Some such classical protocols include the Ovako Working Analyzing System ("OWAS"), the Rapid Upper Limb Assessment ("RULA") and the Rapid Entire Body Assessment ("REBA").

The Ovako Working Analyzing System (OWAS) is a practical method for identifying and assessing working postures. This method is based on a protocol of postures (see FIG. 1) that should be filled out during observations of real situations or watching videos of working activities. The protocol assesses the positioning of the back (4 typical positions), arms (3 typical positions) and legs (7 typical positions), and also considers the loads and forces applied during performance of an activity. The result is a score that indicates the severity of the situation and suggests, if it is necessary, corrective measures to reduce workers' exposure to risks. One advantage of this known method is that it can be used in a variety of situations and does not require any invasive equipment. However, results are sometimes poorly detailed and do not allow the reconstruction of the steps of a persons' actions during the activity.

Rapid Upper Limb Method Assessment ("RULA") was developed in 1993 by Institute for Occupational Ergonomics. It is a survey method used in investigations of ergonomic workstations that assesses biomechanical and postural loading of the body especially regarding injuries on the neck, trunk and upper limbs. It provides a score of a snapshot of the activity as part of a rapid screening tool. The main objective of this method is to assess the exposure of workers to risk factors at work, by using diagrams of body postures and three tables of scores (see FIGS. 2A, 2B) that considers: number of movements, static muscle work, strength, work postures for certain equipment and furniture and working hours without a break. The evaluation method is carried out from observations of work activities, taking into account the measurement of angles of each adopted posture, period and duration of a particular position.

Rapid Method Entire Body Assessment ("REBA") analysis identifies musculoskeletal risks through a sensitive postural analysis in a variety of tasks. The tool divides the body into segments that are analyzed individually in relation to the planes of movement. The result of this method is a score for muscular activities caused by dynamic postures, static postures, rapidly postural changes and unstable postures.

While such techniques can be very useful, they generally do not allow reconstruction of the steps of action. In addition, they do not allow the reconstruction of steps of action in a digital human simulation environment using a digital manikin.

Some commercial systems are also used to capture and/or analyze a particular action, attitude or behavior, or a sequence of these, over time. They are called chrono-analysis software. Example software packages include: Captiv-L2100 and Captiv-L7000 (teaergo.com), Observer® XT (www.noldus.com) and Actogram Kronos (actogram.net).

Captiv-L2100 is task analysis software that creates graphics of activity, durations and some statistics through observation of a video it is possible to. The observation of the object of study is made using a protocol that is developed by the user before the analysis. Captiv-L700 is a tool for objective evaluation that synchronizes acquisition of videos images and sensors measurements with wireless solutions, i.e., it is an invasive technique. The focus of this software is industrial ergonomics.

Using Observer XT, behavior and physiological responses can be studied together. The analysis of data often begins with visualizing the event log, one or more videos, and physiological data streams. The physiological data is acquired using sensors and can be imported to the software and then visualized along with the video. The video is analysed according to a coding scheme that is designed by the user and determine what him can do with the data at later stages. The Observer XT also offers descriptive statistics of the coded behavior. Among the possible output are tables of frequencies, durations and other statistics, interaction matrices, and transition matrices. Pocket Observer offers great flexibility and is fully compatible with the Observer XT. It combines the features of The Observer XT with the portability of a handheld computer. The focus of this software is behavioral psychology.

Actogram Kronos is intended to treat records of behavioral observations and digital measurements. The applicative can compare a specific activity in situations that differ, for example the type of tools used or in other cases, in which factors may vary during a sequence. Protocols description must be designed before the data analysis. A protocol description is a table that defines the observable to be considered in treatments.

While such techniques are useful, further improvements are possible and desirable.

Example non-limiting technology herein provides a system and method for analysis of steps of action of a person in activity in an environment with potential occlusion and without the need to use of invasive equipment. Non-limiting implementations use posture registration and postural analysis based on an observation protocol that allows reconstruction, in a digital human simulation environment, of the adopted postures observed in a real time situation or by video.

Aspects of the technology herein relate to a noninvasive observation system and method for postural analysis integrated with a database and a digital human simulation environment, applied to the integrated analysis of comfort criteria.

Example non-limiting technology aspects herein provide a system and a method for observing, capturing and modeling the actions developed for a person performing an activity that aims to reproduce in a digital environment all the dynamic of activity. Through this reconstruction it is possible to create a database of typical and atypical postures associated with different activities and determine dimensional parameters.

An example non-limiting system and method for observation, postural analysis and reconstruction are used to reconstruct the steps of a person's action along an activity, reconstructing each posture adopted in time by the person and associating it with the environment and the positions of the objects that the person is manipulating. Such reconstruction can be accomplished by starting with observing a video or a real time situation.

An example non-limiting system generates a group of quantitative data: types of adopted postures, the number of actions and postures necessary to complete the activity, biomechanical and kinematical analysis of each posture, the spent time proportion for each adopted posture and activity, which postures that were most adopted, the main strategies adopted as this person is handling an object or environment, dimensions, volumes and area occupied by the person during the performed activity.

According to an example non-limiting posture observation protocol, each posture adopted by a person performing a specific activity is reconstructed in a digital environment using the available technology of digital human simulation.

One example non-limiting posture observation protocol is developed from pilot observation of some people performing peculiar activities that could be analyzed in large scale. From these observations it is possible to recognize the main movements of each body part and create a database of body parts postures cataloged by numbers. The association of different postures of a body part results in a complete posture. During the observation process it is possible to identify new postures and consequently the non-limiting method is capable of allowing the addition of new postures into the protocol in order to increase the database of postures.

An example non-limiting system and method for observation, postural analysis and reconstruction comprises:
  a) A noninvasive observation of a person's action;
  b) Identification of the relative position;
  c) Registration of the adopted postures of a person in activity (members' position and objects);
  d) Combination of each body's part (head, torso, arms, legs and feet) selected in the observation step in order to create a posture;
  e) Record of each instantaneous posture;
  f) Reconstruction of the action with respect to time.

An example non-limiting system and method provides noninvasive observation of a video or a real time situation and registration of the adopted postures of a person in activity, without needing to use any apparatus or equipment or sensor that needs to be placed on the object of observation.

The example non-limiting observation is supported by a protocol, in which the postures, objects, environment conditions and actions are identified in a set of possibilities defined previously. The observation protocol can be a paper form or an electronic version of this form installed in a regular computer or person device.

The example non-limiting reconstruction algorithm combines each body part (head, torso, arms and legs/feet) selected in the observation protocol in order to create a posture. Likewise, the non-limiting algorithm also records the position of objects and other environment conditions. The postures, objects and environment conditions generated from the observation protocol are used to create a digital image of each adopted posture, using available digital human simulation software and a CAD system.

In one non-limiting arrangement, the steps of action are constructed using digital images of each adopted posture extracted from a database of typical and atypical postures. The result is a representation of the dynamic of the activity in a three-dimensional environment. The aim of the three-dimensional representation is to determine dimensional parameters through the identification of volumes and areas occupied by a person during the steps of action of each activity.

The example non-limiting reconstruction algorithm also registers the time that each posture starts and ends and generates a report at the end of observation with statistic data statistical analysis, correlations, charts the steps of action and others quantitative data: number and types of postures adopted, the number of actions and postures necessary to complete the activity, position of objects and environment conditions, biomechanical and cinematic analysis of each posture, the percentage of time of each adopted posture and activity, postures that were most adopted, the main strategies used during a manipulation of an object or environment, dimensions, volumes and area occupied by the person during the performed activity.

Further example non-limiting features and advantages include a system and method that:
  Enables identification of temporally-relevant activities or postures
  Enables the identification of geometries of seats and other objects and equipment that support adequately the performance of an activity or specific posture and that are temporally relevant
  Enables the identification of the occupied volumes and dimensions necessary to carry out an activity/posture specific and that are temporally relevant.
  Enables the definition of design parameters for the geometries of the seats, positioning of controls and accessories, and spaces inside the vehicles considering the set of activities/postures assumed by the person (a passenger, for example).

BRIEF DESCRIPTION OF THE DRAWINGS

These and other features and advantages will be better and more completely understood by referring to the following detailed description of exemplary non-limiting illustrative embodiments in conjunction with the drawings of which:

FIG. 1 is an example prior art Ovako Working Analyzing System (OWAS) protocol;

Figure 2A:
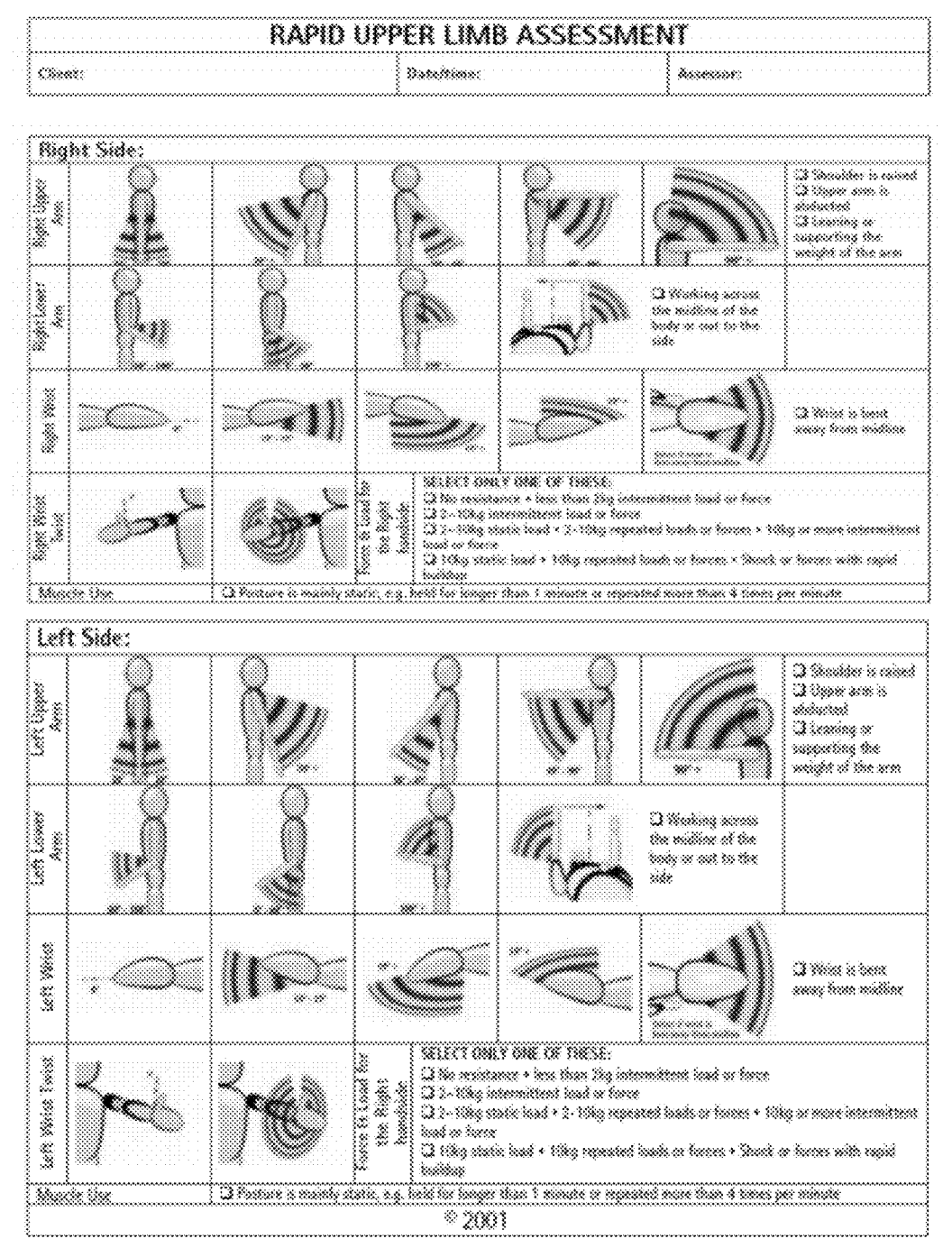

FIGS. 2A, 2B are an example prior art Rapid Upper Limb Method Assessment (RULA) chart;

FIG. 3 is a block functional diagram of an exemplary illustrative non-limiting system;

FIG. 4 is an example non-limiting posture observation protocol;

FIG. 5 is an example non-limiting desktop version of a posture observation protocol;

FIG. 6 is an example non-limiting mobile device version of a posture observation protocol;

FIG. 7 shows example non-limiting steps of action;

FIG. 8 shows example non-limiting postures and activities with respect to time;

FIG. 9 shows example non-limiting volumes of postures; and

FIG. 10 shows example areas created from volumes of postures.

DETAILED DESCRIPTION

Figure 2B:
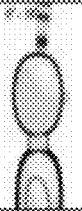

The non-limiting technology herein provides non-limiting systems and methods that enable observation, capturing and modeling of the actions developed and postures adopted for a person performing an activity that aims to reproduce in a digital environment all the dynamic of activity.

One non-limiting exemplary embodiment of the system and method for observation, postural analysis and reconstruction comprises the observation of the activities performed by a passenger during a commercial airline flight, however the system and the method of guidance applies to guidance of any activity performed by a person.

Observation of a video or a situation occurring in real time (see FIG. 3) can be made according to a observation protocol that consists of a postural analysis tool, based on a set of pre-defined postures divided into body segments, positioning of objects and equipment and environmental conditions for a specific activity. The beginning of the observation starts with the characterization of the initial posture of the person, the objects and equipment used and description of environment conditions. The specialist should take note, according to the protocol, after each change of posture, difficulties and successes in carrying out the activity, and unusual situations.

The observation protocol can be a print spreadsheet that the specialist fulfills manually (FIG. 4) or software composed of mobile and desktop versions (FIGS. 5, 6) that automates the process of recording the postures. In this particular example shown in FIG. 4, there are 9 different postures for the head, 9 different postures for the trunk, 19 different postures for the arms, and 19 different postures for the legs and feet. Pattern matching can be used to match the subject's current head/trunk/legs & feet postures with the example posture observation protocol. The posture observation protocol further includes six different patterns for the environment (e.g., seat inclination) that can also be noted using pattern matching and similarly recorded.

After the observation, it is possible to use the postures recorded using the observation protocol to reconstruct the steps of the action of the activity analyzed considering the position of the used equipment and objects that composes the environment. For the reconstruction it is possible to use a CAD environment with a virtual manikin. (see FIG. 3)

FIG. 7 shows an example of a reconstruction of a passenger during a short flight. As can be seen, each square illustrates a different posture adopted by the passenger during the flight and its associated denomination (L1, R1, R2, R3, R1, R4, R5, D1, O1, C1, C2, C3, R6, R7, R8, R9, O2, R10, R11). The denomination was given according to the number of posture associated to each activity. For example, R1 was the first posture adopted by the passenger during the activity of resting. Similar postures are coded similarly (see multiple occurrences of R1), and similar activities are also coded similarly (e.g., L, C, D, O, R).

The analysis of the steps of action generates a graph that shows different adopted postures and their duration according to the performed activity, as can be seen in FIG. 8. Observe that the line of each activity is divided into the adopted postures according to their denomination.

FIG. 8 summarizes the results of table 1 below illustrating the percentage of time a number of adopted postures for each activity during the analyzed situation. In more detail, FIG. 8 illustrates the duration of each activity, the percentage of time for each one in relation of the total time and a number of adopted postures for each activity during the analyzed situation (see FIG. 3).

TABLE 1

Quantitative analyses

| Activities | Duration (min) | % of total time | Number of postures |
|---|---|---|---|
| Read | 1 | 3 | 1 |
| Rest | 22 | 67 | 11 |
| Sleep | 1 | 3 | 1 |
| Look at window | 5 | 15 | 2 |
| Talk | 4 | 12 | 3 |
| Total | 33 | 100 | 18 |

The next step of the example non-limiting method consists of the creation of the dynamic of the steps of action or volume of postures. The volume of postures represents the space occupied by the person during the action of an activity, as can be seen in the FIG. 9.

Through the volume of postures, it is possible to compare volumes of different people performing the same activity, determine dynamic elements related to the activity, occupied areas and dimensional aspects of objects. FIG. 10 illustrates the areas created from the volume of postures of FIG. 9. These 2D areas in each of three orthogonal directions are obtained using conventional calculations to obtain area dimensions in $m^2$.

Thus, the example non-limiting system allows a noninvasive observation of a video or a real time situation and registration of the adopted postures of a person in activity, without requiring use of any apparatus or equipment or sensor that needs to be placed on the subject or object of observation. Through reconstruction of actions, it is possible to create a database of typical and atypical postures associated with different activities and determine dimensional parameters.

Example Non-Limiting Observation Protocol

The example non-limiting system has a posture observation protocol, which consists of a postural analysis tool, based on a set of pre defined postures divided into body segments, positioning of objects and equipments and environments conditions for specific activities, which are also listed in the protocol. It can be developed from a pilot's observation of some people performing peculiar activities inside an aircraft, for example. From these observations, it is possible to recognize the main movements of each body part and create a database of body parts postures cataloged by numbers. The protocol contains for example postures that represent the minimum and maximum range of motion for each joint and intermediate postures between them. The association of different postures of body parts results in a complete posture. The example non-limiting protocol can be modified for adding new postures, objects and activities. For adding new postures, initially it should be identified what postures will be included, through observation of activities. It is possible to take photos to help this process. After the observation, the photos can be integrated into software that translates it in postures of head, arms, legs and trunk.

It is possible to position a manikin in the posture desired. For each part of body, the angles for all the joints can be extracted. The images generated by the postures that are reconstructed by appropriated software, for example RAMSIS, can be translated into this software's language. All the data about the joints can be filed or recorded, in order to use it in the reconstruction process.

As discussed above, the observation protocol can be a print spreadsheet that the specialist fulfills manually (see e.g., FIG. 4) or software composed of mobile (see e.g., FIG. 6) and desktop versions (see e.g., FIG. 5) that automates the process of recording the postures. The desktop version can be used when there is a possibility to record the actions and analyze them after the movement is complete. The example non-limiting mobile version (FIG. 6) can be used without records, when the observation is made in real time. In this case, the software can be inserted in a palmtop, cell phone or other mobile electronic device.

During the observation process made by desktop version, it is possible to identify new postures or activities and the method is able to add new postures into the protocol in order to increase the database. For mobile desktop, when a new posture is identified, the observer can describe it in the line comments. In the mobile version, the software contains a chronometer that is universal and should be set; in other words, an initial situation containing the position of each part of body and each element of environment should be determined for starting the analysis. For desktop version, the time of analysis is the same of the time of video and it is possible change the speed according the observer needs. For both versions it is also possible discard any record that has been done wrong and there is a tool (circumference) that advises the specialist if the posture was registered, for avoiding mistakes in the observation process. Both versions also contain a counter that shows the total number of postures adopted by the observed person.

In one example non-limiting implementation, the result of this analysis is a txt file that contains information such as: data and hour of observation, total number of postures, postures adopted in each activity and the time that the person remained in each one, the position of mainly objects of environment (seat, table) and the comments about the analysis. At the end of analysis, the specialist should save the report and insert passenger and flight data, for example. This "txt" file can be used to open an analysis that had already been made to generate the reconstruction of the course of action or some quantitative analysis.

In order to generate a digital image of each adopted posture, it is possible to create or provide an API application that converts the information registered in the "txt" file in a format that can be read by the digital human simulation software.

Example Non-Limiting Reconstruction Algorithm

An example non-limiting reconstruction algorithm uses the "txt" file to combine each body part (head, torso, arms and legs/feet) selected in the observation protocol in order to create a posture, as can be seen at the FIG. 7 and discussed above. Likewise, the algorithm also records the position of objects and others environment conditions. The postures, objects and environment conditions generated from the observation protocol can be used to create a digital image of each adopted posture, using available digital human simulation software and a CAD system. The API application also adjusts the manikin when there is some collision or lack of information.

The non-limiting reconstruction algorithm also registers the time that each posture starts and ends and generates a report at the end of observation with statistic data statistical analysis, correlations, charts the steps of action and others quantitative data: number and types of postures adopted, the number of actions and postures adopted in each activity, position of objects and environment conditions, the percentage of time of each adopted posture and activity, postures that were most adopted, the main strategies used during a manipulation of an object or environment, dimensions, volumes and area occupied by the person during the performed activity.

The next step is the generation of a full reconstruction in a virtual environment as a representation of all observed movements and postures. The result is a representation of the dynamic of the activity in a three-dimensional environment as shown and FIG. 9 and discussed above.

Summarizing, the non-limiting system and method for observation, postural analysis and reconstruction comprises a three-dimensional representation to determine dimensional parameters through the identification of volumes and areas occupied by a person during the steps of action of each activity, to provide:

a) A noninvasive observation of a person's action;
b) Identification of the relative position of each body part;
c) Registration of the adopted postures of a person in activity (members' position and objects) on a computer by using a posture observation protocol;
d) Combination of each body's part (head, torso, arms, legs and feet) selected in the observation step in order to create a posture;
e) Record of each instantaneous posture;
f) Reconstruction of the action along the time;
g) Identification of the occupied volumes and dimensions necessary to carry out an activity/posture specific and that are temporally relevant.
h) Determine objective measures that will be useful in the design of spaces.

While the technology herein has been described in connection with exemplary illustrative non-limiting embodiments, the invention is not to be limited by the disclosure. The invention is intended to be defined by the claims and to cover all corresponding and equivalent arrangements whether or not specifically disclosed herein.

We claim:

1. A computer-operated method of analyzing individual activities using a processor that automatically processes received input data, the method comprising:
   recording observed posture and activities of a subject;
   characterizing the subject's recorded posture and activities based on a posture observation protocol;
   storing the characterized posture and activities in a computer data file;
   using a processor coupled to the computer data file, reconstructing the subject's posture and activities over time based on the computer data file;
   using the processor, ascertaining based on the reconstructing, the subject's activity/movement volume in the space the subject occupies over time as the subject moves for a certain amount of time; and
   determining areas in the space that the subject occupied over time from the ascertained volume.

2. The method of claim 1 wherein the characterizing includes characterizing the subject's head, trunk, arms and legs and feet postures separately using a coding scheme.

3. The method of claim 1 wherein the characterizing includes characterizing the position of moveable objects in the subject's environment.

4. The method of claim 1 wherein the characterizing includes using a desktop computer to match video-recorded subject posture with predetermined patterns in a database.

5. The method of claim 1 wherein the characterizing includes real time characterizing of the subject's posture with a handheld device.

6. The method of claim 1 wherein the characterizing includes real time characterizing of the subject's posture with a print spreadsheet.

7. The method of claim 1 wherein ascertaining volume includes using computer-generated 3D object representations to ascertain the total volume in space the subject occupies over the certain time.

8. A computer system for analyzing individual activities including a processor that automatically processes received input data, the system comprising:
   an input means that captures the posture and movement of a subject;
   a processor coupled to the input means that characterizes the subject's posture and activities based on a posture observation protocol and stores the characterized posture and activities in a computer data file;
   a reconstructor that reconstructs the subject's posture and activities over time based on the computer data file, ascertains based on the reconstructing, the subject's activity/movement volume in the space the subject occupies as he moves for a certain amount of time; and determines areas in the space that the subject occupies over time from the ascertained volume.

9. The system of claim 8 wherein the processor characterizes the subject's head, trunk, arms and legs and feet postures separately using a coding scheme.

10. The system of claim 8 wherein the processor characterizes the position of moveable objects in the subject's environment.

11. The system of claim 8 wherein the processor comprises a desktop computer that matches video-recorded subject posture with predetermined patterns in a database.

12. The system of claim 8 wherein the comprises a handheld device that characterizes the subject's posture in real time.

13. The system of claim 8 wherein the reconstructor ascertains volumes in space includes using computer-generated 3D object representations to determine the total volume in space that the subject occupies over time.

14. A computer system for analyzing individual activities comprising:
   an input device that captures the posture and movement of a subject;
   a memory device that stores information;
   a processor coupled to the input device and the memory device, the processor being configured to characterize the subject's posture and activities based on a posture observation protocol and to store the characterized posture and activities in the memory device; and
   a reconstructor that (a) reconstructs the subject's posture and activities over time based on the stored characterized posture and activities, (b) ascertains based on the reconstructing, the subject's activity/movement volume in the space the subject occupies as the subject moves for a certain amount of time; and (c) determines areas in the space that the subject occupies over time from the ascertained volume.

* * * * *